US005466425A

United States Patent [19]

Adams

[11] Patent Number: 5,466,425

[45] Date of Patent: Nov. 14, 1995

[54] BIOLOGICAL DECONTAMINATION SYSTEM

[75] Inventor: Billy J. Adams, Usk, Wash.

[73] Assignee: Amphion International, Limited, Dublin, Ireland

[21] Appl. No.: 273,102

[22] Filed: Jul. 8, 1994

[51] Int. Cl.[6] .................... C02F 1/32; B01J 19/12

[52] U.S. Cl. .................... 422/186.3; 422/20; 422/22; 422/24; 422/186; 422/186.04; 422/900; 422/907; 422/127; 210/243; 210/748

[58] Field of Search .................... 422/20, 22, 24, 422/186, 186.04, 186.3, 900, 907, 127, 128; 210/243, 748

[56] References Cited

U.S. PATENT DOCUMENTS

| | | | |
|---|---|---|---|
| 5,198,122 | 3/1993 | Koszalka et al. | 219/748 |
| 5,304,302 | 4/1994 | Bossert | 210/222 |
| 5,376,281 | 12/1994 | Safta | 210/748 |
| 5,380,445 | 1/1995 | Rivard et al. | 210/748 |
| 5,384,032 | 1/1995 | de Souza | 210/104 |
| 5,393,417 | 2/1995 | Cox | 210/96.1 |

*Primary Examiner*—Donald P. Walsh
*Assistant Examiner*—Daniel Jenkins
*Attorney, Agent, or Firm*—Pillsbury Madison & Sutro

[57] ABSTRACT

A system for reducing biological organisms in a liquid effluent to non-viable organic molecules that includes: a stunning chamber that applies a voltage potential across biological organisms to break cell membranes and disable the defense mechanisms of vital organisms to ultraviolet radiation; a cavitation chamber to physically destroy any remaining membranes of biologicals in the effluent that may play host to vital organisms or allow such to hide therein, the action of the stunning and cavitation chambers releasing interferons; and a molecularly implanted stimulated emitter (MISE) chamber in which high levels of ultraviolet radiation are applied to virions and spores that remain at frequencies that are readily absorbed and operate to disassociate any viable DNA and RNA strands remaining, to thereby cause "death". Prior to the stunning chamber, preferably the effluent has any large solids therein, settled, floated or filtered out. When potable water is to be produced, heavy metals and other common inorganic contaminants are also removed. The resulting effluent is pulsed through the stunning, cavitation, and MISE chambers to gain maximum effect thereof. Once the DNA and RNA strands have been disassociated in the MISE chamber, the environment of the downstream flow is controlled to prevent reassociation of organic molecules into viable DNA or RNA strands by either diluting the output of the MISE chamber to such an extent that organic molecules are unlikely to recombine, or when drinking water is to be produced, by filtering the organic filtering the organic molecules out for cosmetic purposes.

40 Claims, 8 Drawing Sheets

BIOLOGICAL DECONTAMINATION SYSTEM

BACKGROUND OF THE INVENTION

Since the 19th Century discovery of the cause of cholera epidemics in London and their prevention through treatment of sewage and other effluent to remove and/or kill organisms within the effluent, many advances have been made in the treatment of organically polluted effluent. Early in the development of water treatment systems, chlorine and other halides were found to have deleterious effects on water born organisms, and chlorine compounds are now commonly used to reduce the number of living organisms in water supplies to reasonably safe levels.

It has also been determined that photonic absorption, such as is possible with high levels of radiation at preferentially absorbed frequencies, can cause total photodynamic inactivation of several bacteriophages. (See R. Hall as cited in General Electric Lamp bulletin LD-14; and M. Luckiesh, "Germicidal Eythermal Energy Research" from D. Van Nostrand Co). When a non-fluorescing organism absorbs a photon, the energy is usually converted into vibrational energy (heat) that raises the internal temperature of the organism. Viral organisms are extremely sensitive to such energy. They are so small that the absorption of very few photons causes their internal temperature to rise to levels that are dangerous to their continued existence. In fact, this form of heat energy within viral organisms, causes viral inactivation when the temperatures there within exceed 100° C.

Photobiologists have discovered absorption curves for various biological parts. For example, proteins normally have peak absorption when exposed to radiated ultraviolet (UV) energy at wavelengths of 300 nanometers (nm) to 280 nm, and ribonucleic acid (RNA) has an absorption peak to radiant wavelengths from 265 nm to 245 nm, with an absolute peak at 253.7 nm. The peak absorption for virions occurs at about 260 nm. 184.9 nm energy is the peak energy used for the breakdown of the hydrogen bond that links the DNA chain and phosphorous bond that links the RNA chain. In addition, application of 184.9 nm UV causes free oxygen molecules in the substance under treatment to add an oxygen atom to form ozone, a proven virion deactivator.

Therefore, sterilizers have been constructed that expose a fluid stream to ultraviolet radiation in the 300 nm to 180 nm wavelength range at an applied power of the 30 Kergs per $mm^2$ or more required to disassociate the deoxyribonucleic acid (DNA) and RNA of viral organisms.

Although with prior art UV sterilization devices, it has been possible to provide UV energy in the correct range of wavelengths and at lethal power levels, such UV devices have had numerous disadvantageous features. First, many have poorly designed flow channels that allow organisms to flow there through without receiving a lethal dose of ultraviolet radiation. Most apply the requisite amount of UV too slowly, thereby allowing viral organisms to produce pigment like molecules that dilute the effect of UV light so that what should be a lethal level, can be withstood. Studies have shown that certain types of viral organisms can produce the UV blocking molecules in as little as ten milliseconds. This means that to apply a lethal dose of UV energy to those virions capable of protecting themselves from UV light, enormous concentrations of UV energy must be provided, since a lethal or at least a debilitating amount of UV energy must be applied and absorbed by every exposed viral organism in less than the first ten milliseconds that the viral organism is exposed. Commercially available intense UV sources used in the prior art devices tend to be narrow frequency devices that are unable to produce lethal intensity at all the peak absorption wavelengths of organisms. The broadband UV energy producing devices that are available produce UV light at relatively low power levels. Examples of these latter sources are UV fluorescent tubes, which produce UV at such low levels that literally hundreds of thousands of lamps are required to treat the effluent in a normal commercial sewage treatment plant.

Over time, when selective kills are attempted, either by chemical means, or inadequate levels or improper wavelengths of radiant energy, microorganisms adapt and become resistant to common killing schemes. Hence, in the case of chlorine, there is evidence that sewer and water supply microorganisms have evolved to tolerate high levels of chlorine. In fact, some now even are able to metabolize chlorine. Not withstanding a reduction in efficacy, chemicals like chlorine build up in an environment, if not poisoning it, changing it in undesirable ways.

Therefore, there has been a need to provide a non-chemical microorganism sterilization process and system for performing the process that allows less than one viable microorganism (including bacteria, virions, fungi, and bacterial spores) to pass therethrough, which can be manufactured relatively economically, and can operate in highly polluted, organic waste water environments as well as being scalable to portable potable water supplies at one extreme and to large city sewage treatment systems at the other extreme.

SUMMARY OF THE INVENTION

The present water treatment system, whether it be large enough for the treatment of an entire city's sewer outflow or just large enough to produce potable water for a military platoon size water supply, includes a particulate filter or settling and floating device to remove relatively large solids, greases and other compounds from the input effluent stream that could dirty and clog downstream components of the system. If potable water is to be the final result of the system, chemical filters are included downstream of the solids filters to remove hazardous inorganic materials such as heavy metals from the input stream. Even after passing through fine filters, an effluent stream is likely to have so many bacteria, bacterial spores, fungi and virions therein, that such effluent can be characterized as an organic soup.

The present invention includes a pulse type pump that moves a predetermined amount of this organic soup into a stunning chamber. In the stunning chamber, a relatively high electric potential is applied across bacterial organisms and spores to fracture cell membranes and slow the natural processes of any viral organisms present.

A typical stunning chamber for a sewer treatment plant includes a plurality of interleaved plates of opposite electrical potential that are spaced far enough apart that microorganisms or small organic or inorganic particles do not wedge there between, clogging the chamber, yet close enough to apply substantial electric potential from end to end across bacteria therebetween. If proper levels of electrical potential are applied in the stunning chamber, no celled organisms emerge therefrom with their cell walls intact. Even if the electric potential is insufficient to cause some of the bacteria to lose structural integrity, it can still be large enough to disorient both the viral organisms living therein and virions present in the fluid so that they are unable to initiate their UV protection mechanisms discussed above.

Intense UV light can be applied immediately after stunning to destroy any viral organisms within or outside the bacteria and the spores through photon absorption and thermal destruction. However, in the present water treatment system, the stunned organisms are usually passed first through a cavitation chamber where they are physically agitated for further disorientation and membrane rupture before exposure to UV radiation. A typical cavitation chamber is one having piezo-electric transducers positioned with respect to the flow to assure that all microorganisms passing therethrough are exposed to high levels of acoustic energy (usually greater than 140 dB at 500 to 1000 Hz).

Whether acoustically tortured or not, the microorganisms in the flow are then pulse flowed to one or more molecularly implanted simulated emitter (MISE) chambers usually provided in tubular form to apply high levels of radiant UV energy to the stream without warning to microorganisms in the pulsed stream. Although in large systems, initial exposure to the UV energy may not be sufficient to kill all viral organisms, it at least further inhibits the viral organisms' ability to mount a defense to lethal doses applied over time thereafter. This "surprise" application is accomplished by sizing the flow passages from the pulse pump to the MISE tube and the flow passages within the stunning and cavitation chambers large enough that pulse flow is maintained with little pressure drop. The outlet of the MISE entry tube usually takes the form of a restrictive orifice, Therefor the flow produced by the pulse pump moves pulse after pulse of fluid into the MISE tube. The pump is coordinated with MISE tube UV exciter control electronics so the MISE entry tube is dark as a fresh volume of effluent is pumped therein. Once the flow has substantially slowed, the UV emitter means of the MISE tube are pulsed at high power levels. Since the viral organisms entering the MISE tube have been stunned and tortured until they are unable to use their UV protection mechanisms, in the present system it is not mandatory as otherwise would be the case, that the viral organisms are "surprised" by their exposure to UV energy.

Generally, the MISE tubes are elongated cylinders. Large industrial MISE tubes for sewer treatment have intense UV sources at each end while MISE tubes for portable potable water supplies can include a concentric UV emitter, such as a fluorescent lamp, extending from end to end down the middle thereof. The MISE tubes are designed to expose any microorganism therein to intense UV radiation. One method to assure complete exposure this is to coat the inner surface of the MISE tube with material that is highly reflective of UV radiation. Magnesium oxide is preferred because it is easy and economical to apply and is highly reflective of the UV energy. The inner surface is then coated with a UV transparent, protective coating for a long life. Since UV sources seldom produce all of the desired wavelengths of enough intensity, UV fluorescent material that absorb wavelengths in over abundance or those having little affectivity and then re-radiate UV at needed wavelengths otherwise weakly present, may be included in the protective coating. Having the outer wall of the tube actually radiate as well as reflect further assures that within the MISE tube, there is no shadow area where microorganisms can hide.

Usually, the outlet of the MISE tube is the minimal flow area for the system so that upstream of the MISE tube outlet, effluent flow is in pressure pulses and downstream it is relatively constant flow. The area around the outlet may be coated with compounds that fluoresce at wavelengths that repel microorganisms, since experiments have shown that a small fractional percent of slightly viable, large mobile virion, were attempting to escape from the outlet.

When the area of the MISE tube adjacent the outlet is Gamma soured and bright blue fluoresced, such virion appear to expend enough energy in moving away from the outlet to become deactivated. Therefore, the natural tendencies of such virion to attempt to avoid UV exposure is used against them and the possibility of outlet escape is eliminated. Suitable electronics coordinate the action of the pump, the stunning chamber, the cavitation chamber, and the MISE tube to efficiently use electrical energy supplied thereto to keep operating costs for electrical power to a minimum. The electronics can be programmed to operate independently or can be controlled through the use of operating personnel control inputs and a display.

Tests of small scale versions of the present system show the synergistic effect of both the MISE tube and stunning chamber because if either is not operating, live organisms emerge whereas if both are operating, less than one live organism ever emerges from the MISE tube. However, the effluent flowing out of the MISE tube may be what can be characterized as a primordial life mixture, full of organic molecules and fragments in such concentrations that it is conceivable they could recombine into viable organisms.

In the case of a small scale water supply system, the output is likely to have relatively few organic molecules therein because normally, the input chosen is not highly concentrated raw sewage. Therefore, the small water supply system output may be just passed to a dark solid state chiller so that little energy is available for recombination of the organic molecules and fragments. Although the output water of the chiller is safe to drink, the organic fragments therein tend to preferentially pass yellow optical frequencies, which give the water an unpalatable appearance. Therefore, the output of the chiller is passed through a carbon filter to remove the organic molecules and fragments so that crystal clear drinking water is delivered.

In a sewage treatment system, multiple settling and float tanks, particulate filters, pumps, stunning chambers, cavitation chambers and MISE tubes may be interconnected by suitable valves so that any component can be taken off line for repair or cleaning, should such be required. The output flow of the MISE tubes without further treatment is suitable as the exhaust effluent of a sewage plant. However, since in most instances sewage plants have their output flow piped a considerable distance before being dumped in a diluting water volume (such as a lake, large river or ocean) a flow channel is provided with a covering that either prevents recombination energy from reaching the organic molecules and fragments, or includes a solar filter that allows only damaging radiation to pass into the flow channel to assure no recombination can occur before dilution where the physical distance between the organic molecules and fragments becomes so large that recombination can not occur.

Therefore, it is a principal object of the present invention to provide a non-chemical fluid treatment system for sterilizing a waste water flow.

Another object is to provide a process to treat waste water, which allows less than one organism to pass viably therethrough, and therefore presents no danger of assisting microorganisms to evolve that are resistant to the system.

Another object is to provide an energy efficient microorganism sterilizing method whose operating principles can be applied to small scale potable water supply systems or large sewage treatment plants.

Another object is to provide a UV microorganism sterilizing device having pre-treatment means that overcome viral organism's responsive defenses to UV radiation.

Another object is to provide a MISE tube, which produces high levels of broadband UV radiation suitable for disrupting the nucleic acids of microorganisms and designed so that any organism passing therethrough is exposed to a lethal dose of UV radiation.

Another object is to provide MISE tubes that are long lasting, easily manufactured, and relatively economical to manufacture and operate in a wide variety of environments.

These and other objects and advantages of the present invention will become apparent to those skilled in the art after considering the following detailed specification together with accompanying drawings wherein:

DETAILED DESCRIPTION OF THE SHOWN EMBODIMENTS

Figure 1:
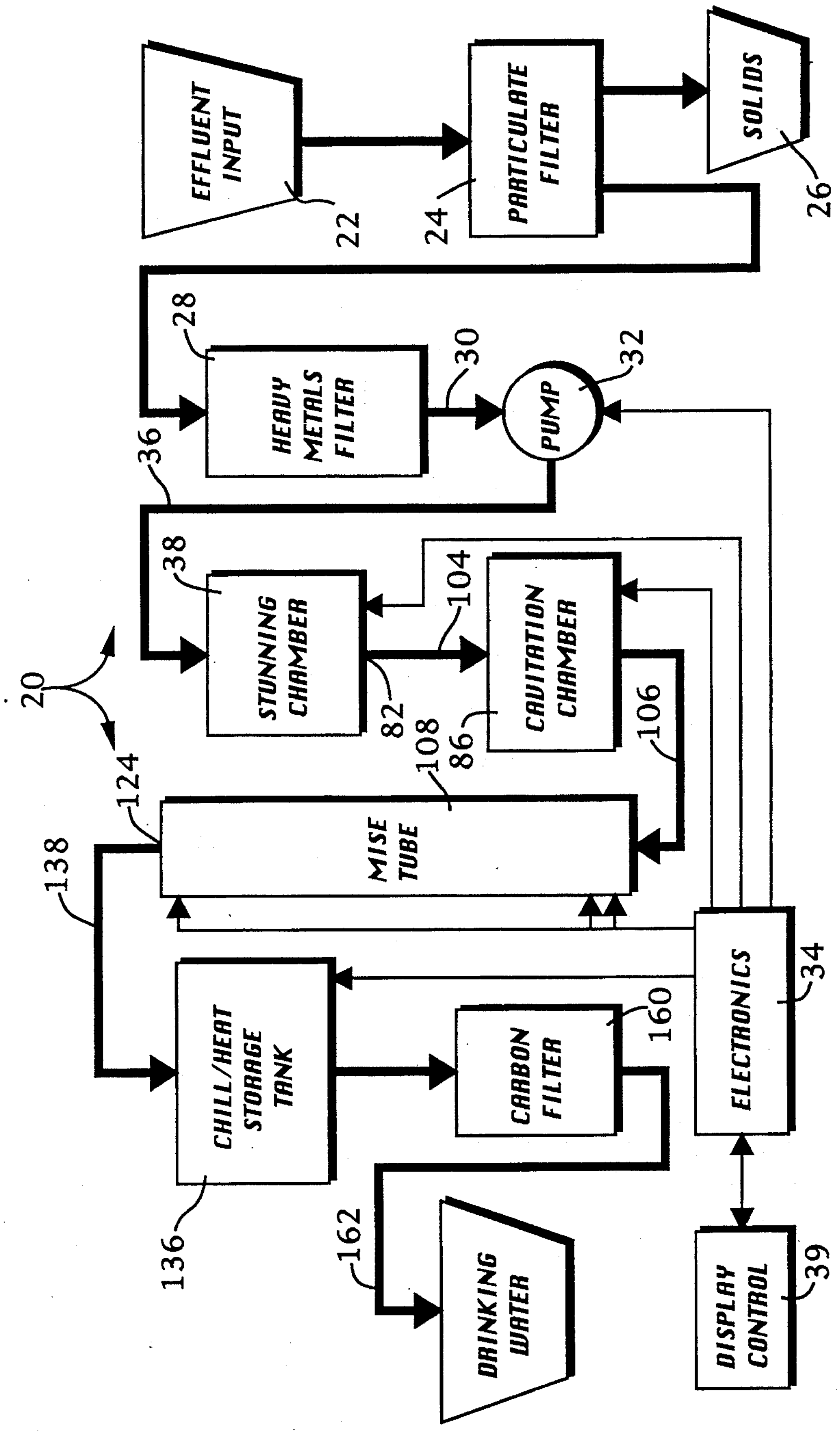
FIG. 1 is a schematic diagram of the present invention as embodied in a small scale potable water supply system.

Referring to the drawings more particularly by reference numbers, number 20 in FIG. 1 refers to a water treatment system for producing drinking water from a affluent input 22 of water of an unknown pollution level. In the system 20 the input 22 may be everything to questionably potable water to a combination of raw sewage and pond scum. Therefore, the input 22 is passed through a particulate filter 24 to remove larger solids primarily to keep them from clogging the flow passages within the system 20. This separates the solids 26 from the water flow. Filter 24 can be any of a number of commercially available filters including a Crane model 1-09-450 filter.

Many input water streams are polluted with other than organic contaminants. Therefore, means such a heavy metals filter or other devices commonly used to remove inorganic contaminants is provided. The output flow 30 from the heavy metals filter 28 provides the input to the organic decontamination portion of the system 20.

The flow 30 is provided as an input to a pump 32. In most instances, the pump 32 is automatically controlled by suitable electronics 34 to produce pulses of fluid flow on its output line 36. Typically, the electronics 38 provides power to the pump on two second intervals. These pulses of flow are input to a stunning chamber 38. A operator control/display 39 can be used to adjust the electronics for different circumstances, or when purging and/or cleaning of the system 30 is required.

Figure 2:
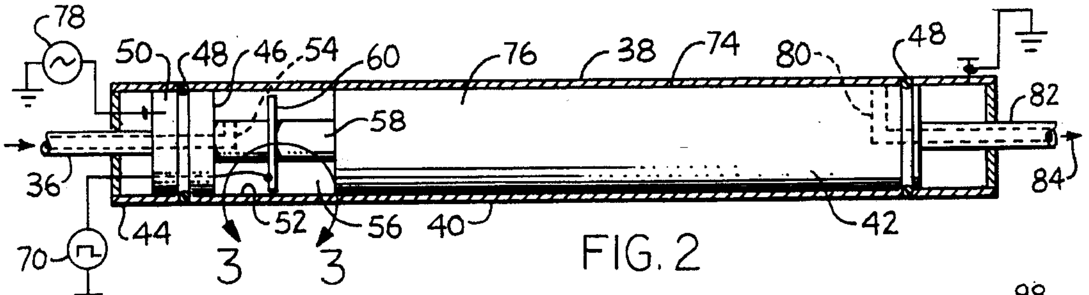
FIG. 2 is a partial cross-sectional view of the stunning chamber of FIG. 1.

The stunning chamber 38 is used to break membranes of celled organisms and bacterial spores within the flow to expose any vital organisms there within which otherwise might be able to hide or be shadowed by cellular structures. The details of a stunning chamber 38 suitable for small flows is shown in FIG. 2.

The stunning chamber 38 preferably is constructed from materials that are resistant to corrosion such as stainless steel. The chamber 38 includes an outer tube 40 within which is positioned a cylindrical center body 42 as shown at the input end 44. The center body 42 includes a connection to the output line 36 from the pump 32. The center body 42 includes a blocking disc 46 that includes a seal 48 about its periphery 50. The seal 48 is electrically insulated and so secure that even virions cannot pass there past either against the periphery 50 of the blocking disc 46 or the inner surface 52 of the tube 40.

The center body 42 includes an input passageway 54 forming a flow passage from the output line 36 into an interior stunning chamber 56 formed by a radially cut out portion of the center body 42 so that a reduced diameter portion 58 is formed.

An insulated disc 60 is mounted on the reduced diameter section 58 of the center body 42. The disc includes a conductive ring 62 about its outer radial periphery 64, the ring 62 having an outer edge 66 closely adjacent the inner surface 52 of the tube 40. The conductive ring is connected by means of a conductor 68 to a source of high voltage pulses 70. As shown, the conductor 68 is sealably passed through the blocking disc 46, however it may be run other places that can provide a fluid tight, electrically isolated passage.

Figure 3:
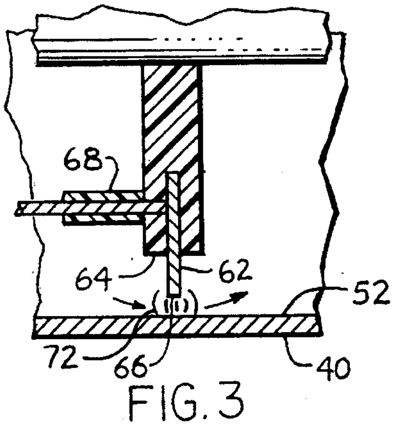
FIG. 3 is an enlarged detail view of the area indicated by the line 3—3 in FIG. 2.

As can be seen in FIG. 3, when the high voltage source 70 is on, a high voltage electric field 72 is established between the inner surface 52 the tube 40, which is shown in FIG. 2 as being grounded, and the outer radial surface 66 of the ring 62. All flow through the passageway 54 is pumped through the area of the electric field 72 which may be left on continuously or only applied when the pump 32 is forcing a pulse of flow there past. The disc ring 62 forms a high energy corona point that is very efficient in applying high potential to adjacent organisms, allowing the system 20 to be operated under battery power. Downstream of the disk ring 62, the center body 42 defines a thin concentric tubular passageway 74 between the inner surface 52 of the tube 40 and an cylindrical surface 76. The center body 42 is connected to a high voltage source 78 of alternating current from the electronics 34. The front outer edge 77 of the cylindrical surface 76 preferably is sharply formed to create a second corona point through which all of organisms present in the flow must pass. The passageway 74 has a thickness large enough to allow the largest virion to pass through but small enough to block an intact cell. Since any blocked intact cellular organism will provide a current path between the inner surface 42 and the cylindrical surface 76, its membranes are very quickly destroyed. To prevent bacteria from passing there through, the thickness of the passageway 74 should be about 254 microns and when bacterial spores are a problem, the thickness of the passageway 74 should be reduced to about 127 micrometers with an increase in diameter to keep the flow resistance thereof at about the same level. The passageway 74 is typically made about 100 millimeters long and is driven at a high enough alternating current to cause nucleic acid ionization as well as general thermal deactivation in the one second minimal time that any organism will spend therein. Alternating current is used to prevent the deterioration of the tube 40 that might occur if direct current was used and to cause viral disorientation. Since the passages in the stunning chamber 38 are small, the flow velocity is very high there through, when compared to flow rates in the components downstream thereof, to be discussed hereinafter.

When the structural membranes of cellular organisms are fractured, their contents, including viral organisms, are dumped into the flow which then passes through the narrow concentric passageway 74 formed between the inner surface 52 of the tube 40 and the outer cylindrical surface 76 of the center body 42 down stream of the interior stunning chamber 56. This breaking of membranes causes the internal nucleic acids of the organisms to also be dumped in the flow causing it to go acidic, which is desirable as an acidic environment is "unfriendly" to most naturally occurring organisms. A second internal passageway 80 connects the passageway 74 to the outlet 82 of the stunning chamber 38. The flow 84 therefrom is acidic and contains few, if any, intact cellular organisms or spores and all the virions remaining are in a disoriented and stunned condition where their ability to manufacture UV protective molecules is disrupted.

Figure 4:
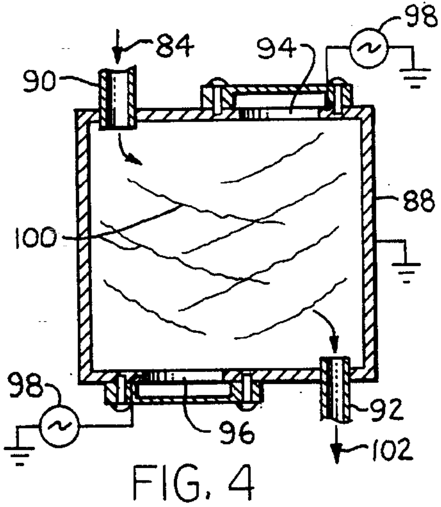
FIG. 4 is a cross-sectional view of the cavitation chamber of FIG. 1.

As an extra precaution to make sure that celled organisms do not survive intact and to provide a cleaning mechanism, the flow 84 then may be passed through a cavitation chamber 86 whose operation is also controlled by the electronics 34. The cavitation chamber 86, whose detail is shown in FIG. 4, includes a water tight housing 88 with an input connection 90 and an output connection 92 attached thereto for flow communication. Piezo electric diaphragms 94 and 96 are positioned facing each other in the housing 88 and are driven by a suitable signal generator 98 in the electronics 38 to produce high intensity acoustic waves 100 that combine in the chamber 86 to produce cavitation in the water there about. The cavitation chamber 86 preferably is made from high silicon stainless steel, such as type 314. This grade of steel is very resistant to water corrosion and due to its almost 50% nickel and chromium composition, it is easy to clean by sonic techniques. The physical dimensions of the cavitation chamber 36 are chosen to optimize the acoustic pressures there within and also so the pressure waves created therein combine in phase at the inlet 90 and outlet 92 for transmission along resonant piping to help keep other components of the system 20 clean and the organisms in the piping disoriented. The acoustic waves 100 are preferably in the frequency bands from 500 to 1000 Hz and from 50 to 70 KHz, since acoustic waves 100 are relatively easy to generate at those frequencies with sufficient intensity to disrupt the membrane of any organism able to withstand the stunning chamber 38. Frequencies at 500 to 1000 Hz are also suitable for resonant matching of the piping lengths required to connect adjacent components for sonic cleaning action. For example, since the velocity of sound in water is about 1430 to 1493 meters per second depending on the temperature, a suitable chamber length for operation at about 733 Hz is about 63.3 nm. The sixth harmonic of longitudinal resonance frequency of a $63.3\times10^{-3}$ m piezo-electric diaphragm equals 71.1 KHz, which provides large separation of the cleaning and cavitation signals.

The diaphragms 94 and 96 can be standard off the shelf, piezo speakers. When the signal generator 98 is connected to the diaphragms 94 and 96 so they are driven in opposite directions with the same signal, the greatest possible pressure differentials appear centrally within the chamber 86. Normally, the signal generators 98 are incorporated within the electronics 34 and may be turned on and off to correspond to pulses of the pump 32.

The connecting piping 104 from the stunning chamber 38 to the cavitation chamber 86 and the connecting dark piping 106 from the cavitation chamber 86 to a molecularly implanted simulated emitter (MISE) tube 108 are about 4 meters in length (about one half of the wave length at 750 Hz) to resonantly couple the acoustic energy of the cavitation chamber 86 therethrough for sonic cleaning of the stunning chamber 38 and the MISE tube 108. The piping 104 and 106, the stunning chamber 38 and the cavitation chamber 86 are made of materials that do not transmit light to literally keep any organisms leaving the stunning chamber 38 in the dark until they reach the MISE tube 108.

Photoprotection is a phenomenon in which irradiation by near UV decreases the sensitivity of certain cells to the UV wavelengths used in the system 20. This protection process is an acquired pigment like plating that reduces the internal UV absorption. To effect a UV shock, the effluent should come from the dark. Within the system 20, a flow delay in the dark piping 104 and 106, and the cavitation chamber 86 is incorporated causing about 10 seconds of time in total desensitizing energy.

Figure 5:
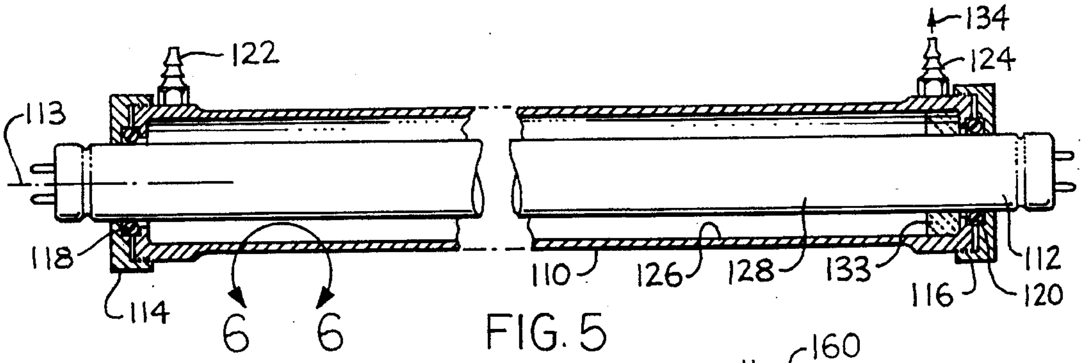
FIG. 5 is a partial cross-sectional view of the MISE tube of FIG. 1.
Figure 6:
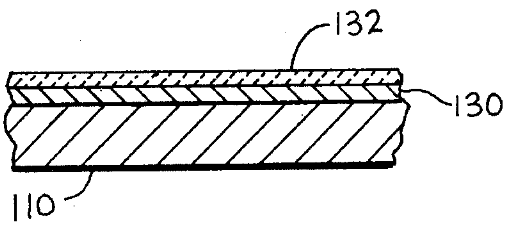
FIG. 6 is an enlarged detail view of the area indicated by the line 6—6 in FIG. 6.

The details of the MISE tube 108 are shown in FIGS. 5 and 6. The MISE tube 108 includes a tubular housing 110 retaining a UV lamp 112 concentrically therein along its longitudinal axis 113 by means of end caps 114 and 116, which in combination with the housing 110 entrap suitable seals 118 and 120 against the UV lamp 112. Preferably, the MISE tube housing 110 is constructed of high silica aluminum extruded tubing. The housing 110 includes an inlet port 122 and an outlet port 124, and with the lamp 112 defines a tubular flow passage 125 through which the pulse flow is maintained. The lamp 112 can be any suitable, off the shelf, low pressure mercury vapor lamp. However, most commercially available power supplies for such lamps are designed on the assumption that lamps driven continuously thereby will be convectively air cooled and continuously driven, and do not allow exploitation of the full UV capabilities of such lamps when they are water cooled and have less than a 100% duty cycle. Therefore the electronics 34 can be designed to provide higher voltage and currents to the UV lamp 112 than is normal practice to cause a more intense sterilizing UV output to be produced. Because of the MISE tube's cylindrical shape, centered lamp 112 and the reflectivity of the tubes inner surface 126, there are only fractional intensity losses. As an example, off-the-shelf circuits and techniques using a germicidal 18 inch lamp only produce about 3.6 watts of 253.7 nm radiation. Therefore, a specialized lamp driver circuit in the electronics 34 is used accounting for a total working 15.6 watts of 253.7 nm flux (15.6 watts is left after some energy is absorbed for fluorescence).

The inner surface 126 of the housing 110 is concentric to the outer surface 128 of the lamp 112 so that no matter what path an organism travels in the tubular flow passage 125 from the inlet 122 to the outlet 124, it is exposed to a lethal dose of UV. To further assure this occurs the inner surface 126, as shown in FIG. 6, includes a highly reflective coating 130 such as magnesium oxide. The reflective coating 130 is covered with a protective coating 132 that includes dopants that absorb UV at the characteristic wavelengths of the mercury lamp 112 and reradiate UV energy at other wavelengths to fill in the UV spectrum produced within the MISE tube 108. Other dopants (such as phosphors) are activated by the alternating potential differences between the plasma in the lamp 112 and the housing 110 to fill in the UV spectrum. Suitable dopants in the MISE coating include: anthranilic acid; benzamidine hyctrochloride; bensene-m- sodium disulfonate; O-chlorobenzoic acid; diphenyl; diphenylanine; hexamethylenetramine triguaiacol; hydrobenzoin; p-phenetole sulfonic acid; and theobromine. UV at 225 nm is needed for virus absorption, UV at 228 nm is needed for pinworms, UV at 253.7 nm is needed for absorption by nucleic acids and UV at 184.9 nm is needed for oxygen and hydrogen bond ionization.

The following process produces a suitable highly reflective inner surface 126 for the housing 110.

After cutting to length and deburring, at least the inner surfaces is smoothed with soft steel wool. The housing 110 is then connected at one end to a positively charged conductive rotator and dipped into a 65° to 72° C. cleaning solution of:

15% Sodium Gluconate $HOCH_2$ [CH (OH)]$_4$ $CO_2$

45 % Sodium Hydroxide NaOH

40% Distilled Water $H_2O$

For 2.5 minutes the housing 110 is fully submerged and rotated at 200 RPM. The process is then halted, the housing 110 reversed end-to-end and then the process is continued for another 2.5 minutes. The housing 110 is then removed from solution and washed in Ethyl Alcohol. To achieve a high degree of UV reflectivity, a thin film of molecularly bonded magnesium is then plated onto the inner surface 126 of the housing 110 by mixing a solution of magnesium gluconate in a Pyrex plating tank of the following ingredients:

60% Magnesium Gluconate {$HOCH_2$ [CH (OH)]$_4$ $CO_2$} Mg*x$H_2O$

29% Ammonium Chloride $NH_4Cl$ 4.5% Ammonium Thiocyanate $NH_4SCN$

5% Magnesium Turnings Mg 1.5% Erbium (III) Oxide $Er_2O_3$

A diluted solution of ethyl alcohol is saturated at 26° C. with this mixture and an anode of magnesium rod is submerged into the solution. Except for the inner surface 126, the housing 110 is externally coated with a liquid tape, electrically connected to a rotating cathode, and then completely submerged into the solution. The anode is spaced from the housing 110. While rotating at a 200 RPM speed, a current is applied between the anode and the housing 110. A slight occasional current reversal is used to strengthen the bond of the plated magnesium to the aluminum inner surface 126. The temperature is maintained at 26° C. The plating process is continued until the interior diameter of the inner surface 126 has decreased by 25 μm. The finished inner surface 126 is then polished with a soft cotton cloth saturated with the following mixture:

60% PEEK

30% Hexamethylenetramine

5% Dimthylxanthine

5% Diphenylamine

Allowing the tube never to dry by adding ethyl alcohol, the mixture is rubbed over the interior plating for 30 seconds rotating the cloth at a rate of 200 RPM. A clean dry soft cotton cloth is then spun through the tube interior at a rate of 1750 RPM for 30 seconds to cause friction heating, polishing to harden the coating. At this time the ends of the finished housing 110 are capped with metal tape ready for its completion at least 24 hours later.

Figure 7:
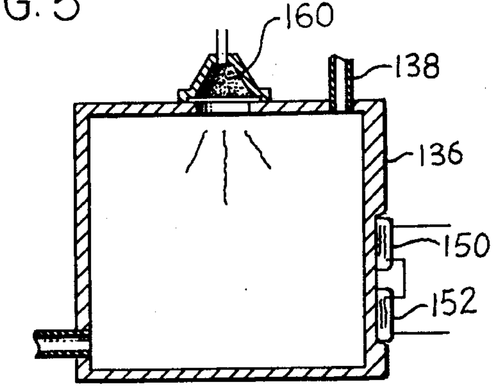
FIG. 7 is a cross-sectional view of the chill/heat storage tank of FIG. 1.

Others have determined that total Photodynamic inactivation of several bacteriophages starts at 30 Kergs/mm$^2$ near 253.7 nm radiation by R. Hull (as cited in General Electric Lamp bulletin LD-14. Also see M. Luckiesh, "Germicidal Eythermal Energy Research" from D. Van Nostrand Co. Apparently this inactivation is caused by photonic absorption forcing the generation of interferons, the cellular proteins produced in response to some stimuli that act to prevent replication of an infectious viral form. When a substance absorbs a photon, the energy is usually converted into mostly vibrational energy (non- fluorescing compounds). This form of "heat energy" will cause inactivation in most viral organisms when allowed to reach 100° C. As shown in FIG. 7, photobiologists have plotted absorption curves for the various biological parts: protein has a peak from 300 nm to 280 nm; and RNA absorption occurs from 245 nm to 265 nm with a maximum absorption at 253.7 nm. The general virus absorption peaks at about 260 nm. As a result of this data for inactivation, the MISE tube 108 is designed to deliver a fairly flat intensity of U.V. radiation from 300 nm to 180 nm with a peak output of 253.7 nm.

Having an energy equivalency of $1\times10^7$ ergs for one joule equalling one watt/sec. and the requirement of 30 Kergs per mm$^2$ for interferon generation resulting in inactivation, a minimum U.V. requirement is calculated to be 3 mJ per mm$^2$.

The MISE tube 108, is a cylindrically contained, bidirectional UV generator with tuned electro-photoluminescing ability. The MISE tube 108 is designed to hold a volume of effluent solution in close proximity between a UVB (300 to 200 nm germicidal) and UVC (200 to 40 nm ionizing) generator (the lamp 112) and a greater than 97% reflective wall surface 126 with a UVA luminescent coating (400 to 300 nm) that is pumped, yielding an increased reflected UV spectrum.

The required UV energy is dependent on experimentally tested total surface area illumination from both wall and lamp surfaces. For an 18 inch low pressure mercury lamp, the active output energy is: 355.6 mm of the lamp length. 25.4 mm is the external lamp diameter therefore the total surface area πdh is:

$$\pi(25.4\ \text{mm})\ (355.6\ \text{mm})=28.38\times103\ \text{mm}^2$$

A minimum of 30,000 ergs are required per square mm so:

$$(28.38\times10^3)\ (30\times10^3)=851.24\times10^6$$

at $1\times10^7$ ergs $J^{-1}$ then:

$$\frac{851.24\times10^6\ \text{ergs}}{1\times10^7\ \text{J}}=85.1\ \text{Js}$$

The emitting/reflected surface is also 355.6 mm in length but it is 38.1 mm in diameter so:

$$\pi(38.1\ \text{mm})\ (355.6\ \text{mm})=42.56\times10^3\ \text{mm}^2=127.7\ \text{Js}$$

A total bi-directional illumination is therefore 212.8 Joule. Hence a measured 15.6 watt delivery system requires a time factor of:

$$\frac{212.8\ \text{Js}}{15.6\ \text{W}}\ \text{or 13.6 seconds}$$

By utilizing an on\off pulsed pump filling from the gravity bottom of the MISE tube 108, a very even, minimum turbidity flow of effluent is accomplished that allows a minimum time of 14 seconds of fluid throughput, as set by experiments for each system 20.

Several photo-physics laboratories have shown that viral buoyancy exists in some virion causing them to float in water. It has also been shown that active virion will migrate away from the blue light portion of the spectrum. Therefore, a specially positioned and enhanced blue fluorescence repeller 133 is included about the general proximity of the outlet 124 of the MISE tube 108 in its protective coating 132. Using the already self contained high photonic energies to cause fluorescence, the blue fluorescence repeller 133 made of a ceramic fluorescent "repeller" consisting of the following weight percents:

| | | |
|---|---|---|
| $CaF_2$ | Fluorspar | 40.00% |
| $U^{238}$ | Uranium | 34.00% |
| LiF | Lithium Fluoride | 15.00% |
| BaO | Barium Oxide | 5.79% |
| $B(OH)_3$ | Boric Acid | 5.00% |
| Er | Erbium | .20% |
| Eu | Europium | .01% |

emits blue 460 nm light. Along with this fluorescing repeller 133, the outlet 124 is made to be the smallest flow passage so that the flow therethrough regulates the total through-put of fluid of the system 20.

Since the electrical pumping must be alternating currents to pass their effects through the dielectric barriers to the MISE tube 108, pumping frequencies produced are chosen to cause resonant chamber cleaning and also to be physically damaging to virion. RNA, DNA and proteins strongly absorb vibrational energy in the range from 34 KHz to 103 Khz. Therefore a constant virion harmonic amplitude of 69 KHz is superimposed onto the lower cleaning frequency of the cavitation chamber 86 at 733 hertz. This chamber frequency generated in the electronics 34 and applied by the piezo diaphragms 94 and 96 can be controlled to match physical changes in chamber manufacture.

Total required harmonic input energy is based on a maximum virion volume of 28 nm at $6.64\times10^{-2}$ Kg each.

$$\text{Chamber Volume} = \frac{\pi C}{4}\ (D^2 - d^2)$$

$$V = \frac{\pi\ (355.6\ \text{mm})}{4}\ (38.1\ \text{mm})^2 - (25.4\ \text{mm})^2$$

$$V = 225.23 \times 10^3\ \text{mm}^3$$

For virion approximation:

$$\frac{225.23 \times 10^3\ \text{mm}^3}{28 \times 10^9}$$

-continued

Count: $\approx 8.04 \times 10^{12}$

Mass: $\approx 53.43$ ng and since they are for the most part water, the total energy to generate an 80° C. increase is:

$$53.43\ \text{ng} \times 80° \approx 4.27 \times 10^6$$

$$(5 \times 10^3)\ (.2389\ \text{J}) = 1.19\ \text{KJs}$$

$$\frac{1.19\ \text{KJs}}{13.6\ \text{s}} = 87.47\ \text{watts}$$

Less the already 15.6 watts of UV absorbed, the necessary 71.87 watts of vibrational energy are left.

Figure 8:
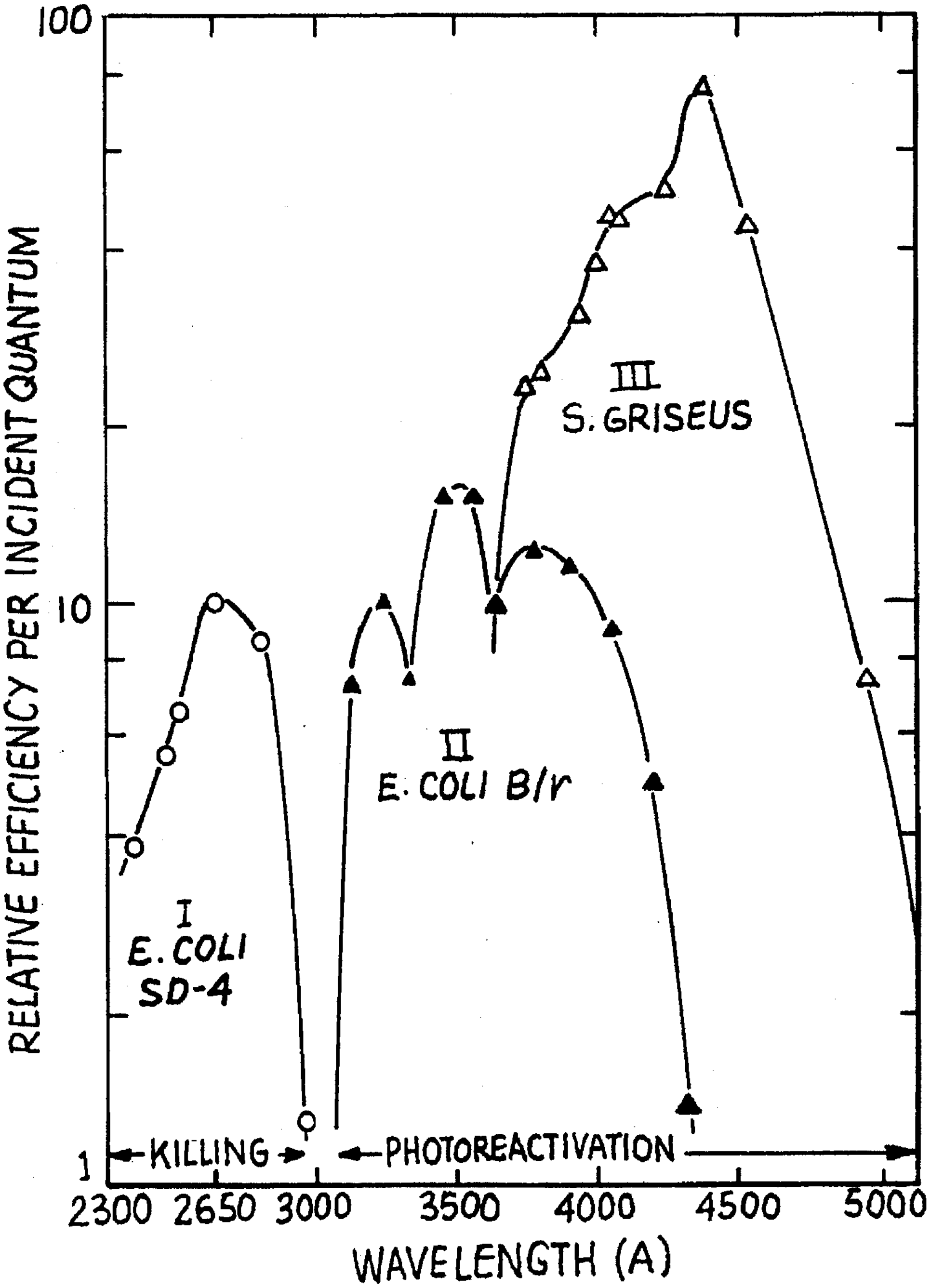
FIG. 8 is a graph of known photoreaction in relation to wavelength and relative efficiency.

The transit time within the MISE tube 108 and UV intensities and frequencies therein are chosen to assure that no viable organism passes out of the output 124 thereof in the output flow 134. However, the flow 134 is a variable mix of organic fragments and molecules that theoretically could recombine into viable organisms if the proper environment and energy is provided. Therefore, the flow 134 is directed to a chill/heat storage tank 136 by means of a dark pipe 138. The details of the chill/heat storage tank 136 are shown in FIG. 8. To eliminate the possibility that the organic fragments and molecules will recombine into viable organisms within the tank 136, the chill/heat storage tank 136 includes Peltier cooling diodes 150 and 152, thermally attached to the tank 136 for clean, quiet chilling. The Peltier cooling diodes 150 and 152 can be used to cool the water stored in the tank 136 or by using the control 39 to reverse the polarity of the current from the electronics 34, they can also be used to heat the water so hot water is available. A long wavelength infrared (IR) source 154 may be included to provide damaging IR radiation into the tank 136 and an ozone generator 156 also may be provided. The IR source 154 is used to irradiate the flow within the storage tank with long wave length IR, which along with ozone produced by the ozone generator 156, disables any repair enzymes and provides a hostile environment to any wandering microbe by forcing oxidation.

After microbe tissue damage that is not completely fatal, a process called photoreactivation can take place. Photoreactivation of bacterial viruses is temperature and energy dependent. This recovery from damage is enhanced by nutrients, warmer waters and radiation in the 300 to 500 nm range as shown in the example graph of FIG. 8 from existing literature. The impingement of the infrared light from the IR source 154 in the pulsed mode can been used to inhibit the enzyme work without appreciable water heating.

The process of microbe inactivation leaves organic fragments and molecules in the water that scatter and absorb different frequencies of light, which usually cause the water appear amber. Psychologically, amber colored water is not particularly palatable and therefore the water from the tank 136 is flowed through a fine carbon filter 160 capable of removing the small organic bits. Such filters are commercially available and usually are filled with activated carbon. Activated carbon is a large surface granular non-crystallized carbon made by low temperature and low pressure techniques so that it has an enormous number of nanometer pores that can capture and absorb non-polar substances. The output 162 of the carbon filter 160 is suitable for use as drinking water.

A one second pump cycle with suitable flow rate can maintain a suitable discharge pressure to assure the ~14 second UV MISE tube time. In the experimental example described above, effective ⅛ by ½ inch output restriction is a composite restriction, working with the back pressure of the carbon filter 160, and only occurs after the water reaches the filter 160. Therefore, if the system 20 is designed to be very efficient to prevent the wasting of energy, it should be primed slowly to make sure that early high flow rates can not sweep viable virions therethrough.

Figure 9:
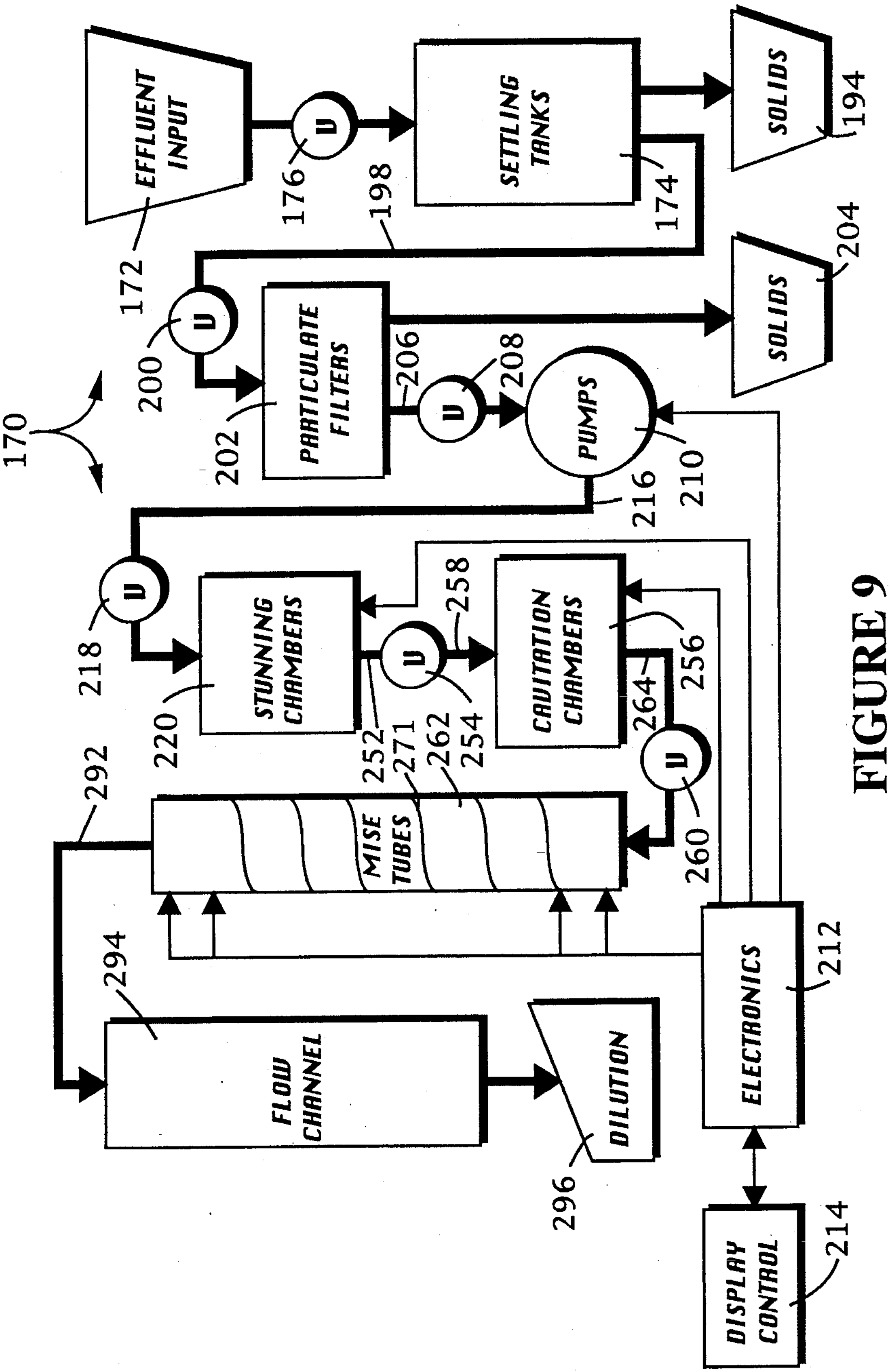
FIG. 9 is a schematic diagram of the present invention as embodied in a large scale sewage treatment facility.

FIG. 9 is a flow diagram of a large scale waste water treatment system 170. The effluent input 172 to such system 170 typically is raw sewage. The effluent is switched between various settling tanks 174 by suitable valves 176, the details of a settling tank 174 being shown in FIG. 10. The effluent input 172 is bottom fed into the tank body 178 preferably surrounded by a virus attractant and xenon kill device 180 such as are known in the art. The tank body 178 is designed to have almost no currents therein allowing sludge to settle to the bottom 181 of the tank body 178 and be removed at a bottom sludge drain 182 by means of a sludge pump 184. Sludge 186 typically is processed by flowing it onto means like the drying belt 188, where the liquid 190 is removed and forced back into the tank 178 by a recycle pump 192. The solids 194 are collected for further processing and disposal. Since some solids float, a sludge scraper 196 is employed about the upper surface of the tank body 178 to gather the floating sludge adding it into the sludge stream 186 for separating as described above. A large percentage of the solids are removed by the settling tanks 174 so that the output flow 198 thereof is relatively clean except for small particles and microorganisms whose density approximates that of water. Valves 200 (shown in FIG. 9) are used to direct the output flow 198 of the settling tanks 174 through one or more particulate filters 202 similar to those used in the system 20 previously described, but larger and adapted for high flow commercial use. Such particulate filters are commercially available. The particulate filters 202 remove fine solids 204 and produce a flow 206 through valves 208 to one or more pumps 210. Preferably, the pumps 210 like those in system 20 are driven by suitable electronics 212 having a display/control 214, so that the flow downstream from the pumps 210, is in pulses. Generally, the pumps 210 produce pulses that are over 10 seconds long. Accounting for the larger size of the downstream components to be discussed hereinafter, the output 216 of the pumps 210 is directed by suitable valves 218 to stunning chambers 220. A suitable industrial stunning chamber 220 for a waste water treatment plant is shown in exploded detail in FIG. 11.

The stunning chamber 220 includes an inlet 222 into a plenum chamber 224, which causes the flow downstream thereof to be relatively evenly created between spaced parallel electrode plates 226 and 228 with the plates 226 and 228 alternating across the chamber 220. The plates 226 are all connected to one electrode 230 while all the plates 228 are connected to another electrode 232. The plates 226 and 228 include seal and insulating areas 234 and 236 at their upper and lower edges respectively so that flow as shown by arrows 238 occurs at right angles between the plates 226 and 228. Any organisms in the flow 238 are exposed to high electric fields, which are created by applying a high voltage potential across the electrodes 230 and 232. The spacing between the plates 226 and 228 is chosen so that no intact cellular microorganism can pass therethrough without contact with at least one plate. Like the stunning chamber 38, stunning chamber 220 breaks the membranes of cellular organisms releasing their interferons and dumping any viral organisms contained therein into the flow 238 for disorientation and disruption of their UV protection mechanisms.

Figure 12:
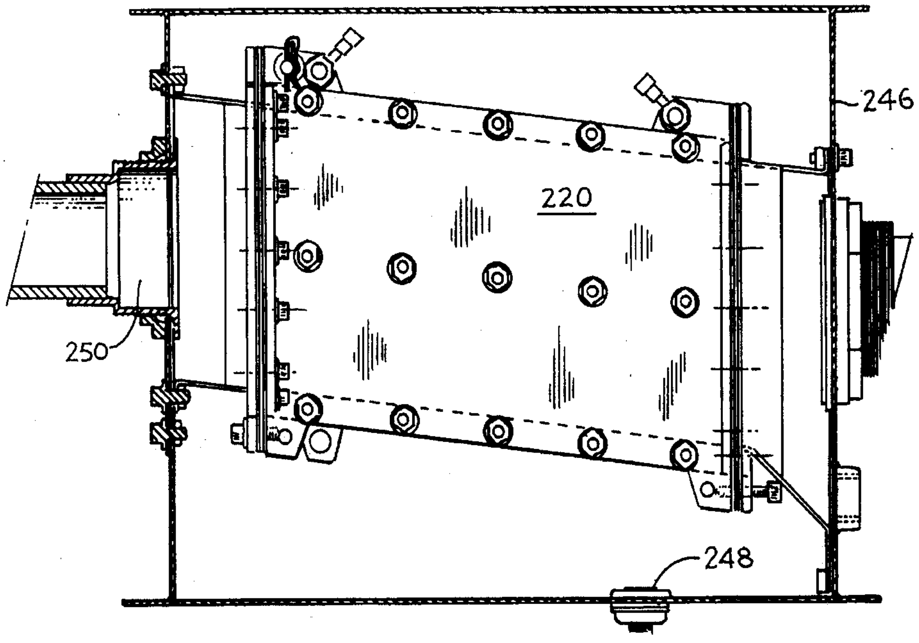
FIG. 12 is a side elevational view of the stunning chamber of FIG. 11 in partial cross-section.

As shown, the stunning chamber 220 includes suitable flanges 240, bolts 242, and insulating spacers 244 to maintain the structural watertight integrity of the chamber 220. As shown in FIG. 12, the stunning chamber 220 may be positioned within an enclosure 246 so that any incidental leaks from the chamber 220 can be collected by a drain 248 and reintroduced into the flow upstream of the pumps 210. Also, as shown in FIG. 12, preferably the stunning chamber 220 is built with a slight upward bias from input 220 to its outlet 250 so that any gases or air transported or generated by the effluent is pumped clear of the plates 226 and 228 by the flow 238 therethrough.

Figure 10:
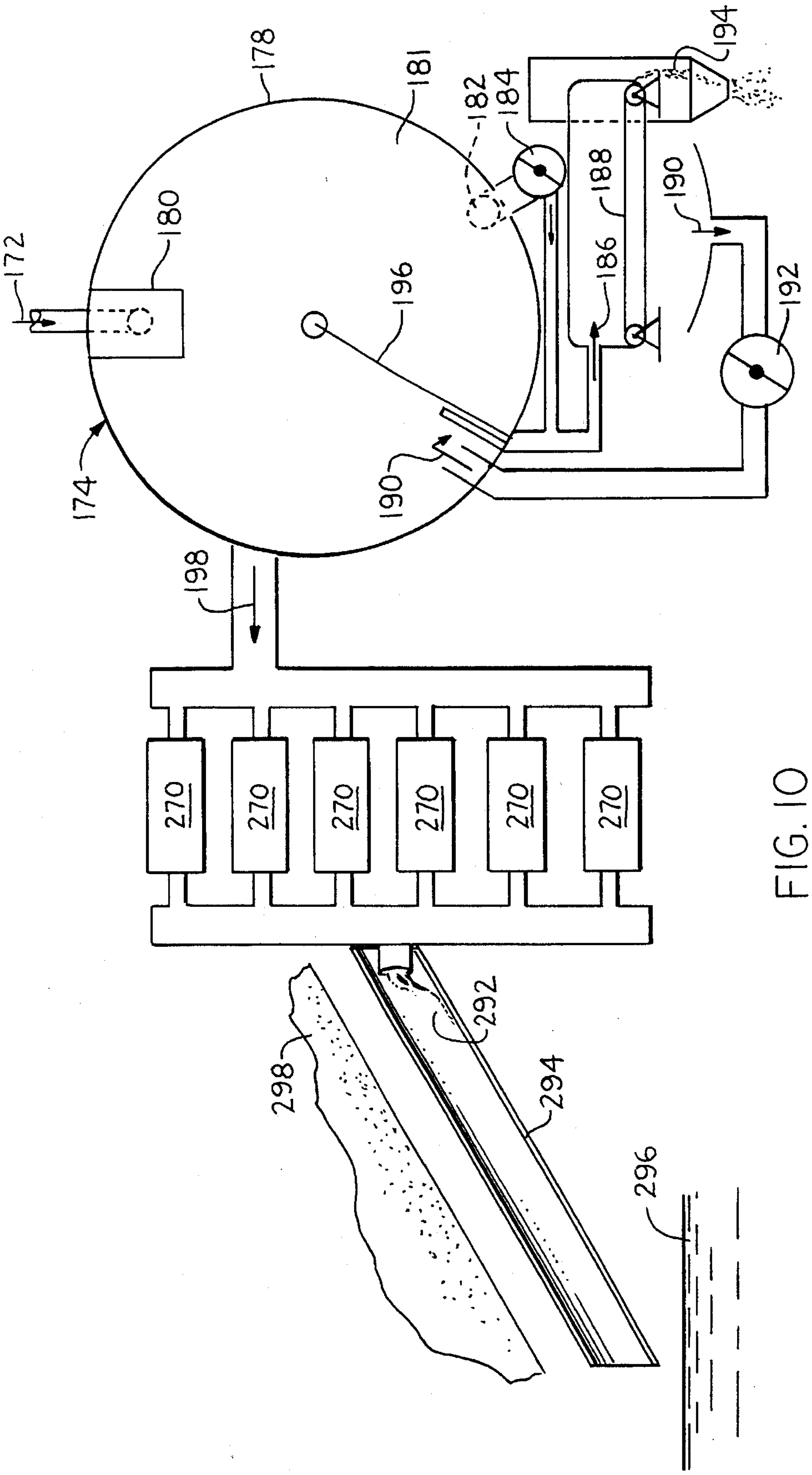
FIG. 10 is another schematic diagram of the present invention as embodied in a large scale sewage treatment facility with the details of a prior art sludge removal tank incorporated therewith.
Figure 11:
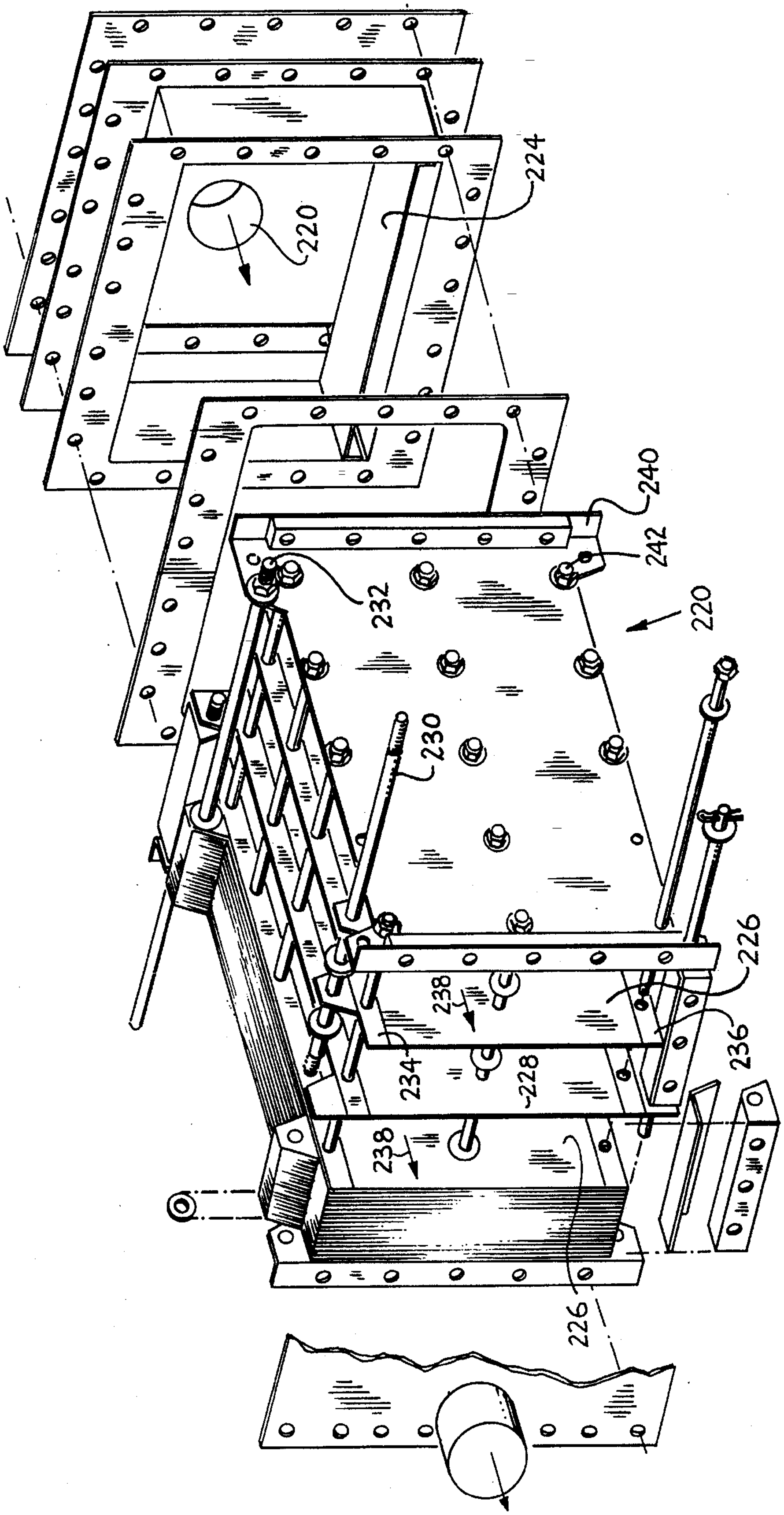
FIG. 11 is an exploded view of a stunning chamber of FIG. 9.

The outlet flow 252 from the stunning chambers 220 is directed by valves 254 to cavitation chambers 256 by means of dark piping 258 which can block any radiant energy from the outside that might allow repair mechanisms of the organisms stunned by the stunning chambers 220, to repair themselves. The cavitation chambers 256 are similar to those described in detail for system 20 with their frequencies adjusted to account for differing resonant line lengths, chamber sizes and flow requirements. Like before, the cavitation chambers 256 are filled with acoustic energy at a cleaning frequency and a destruction frequency. The lower cleaning frequency being resonantly piped to the stunning chambers 220 and through valves 260 to MISE tubes 262 downstream thereof for cleaning and high frequency sound for disruption and disorientation of the microorganisms in the flow. The output 264 of the cavitation chambers 256 is directed by the valves 260 to a plurality of MISE tubes 262. A typical layout of MISE tubes 262, cavitation chambers 256, stunning chambers 220, pumps 210, and particulate filters 202 are shown in FIG. 10 by the modular blocks 270. This modular configuration downstream of the settling tanks 174, allows a module 270 to be taken off line for maintenance or emergency repair, while the remainder of a waste water treatment facility is operated normally.

MISE tubes 262 for industrial or waste water treatment facilities must be much larger than those shown in system 20. For example, the plant shown in FIG. 10 might be called upon to have a gravity flow throughput of as much as three million gallons a day, whereas the system 20 might have a maximum throughput of one hundred gallons a day.

Figure 13:
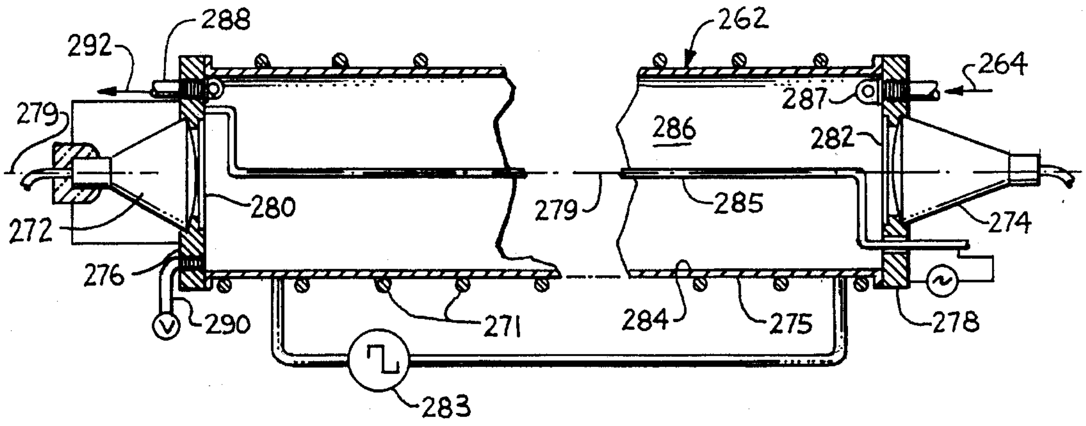
FIG. 13 is a cross-sectional view of the MISE tube of FIG. 9.

A typical MISE tube 262 is shown in FIG. 13. The prime difference between the MISE tube 262 and the MISE tube 108 is a matter of scale, the addition of a coil 271 to produce a strong magnetic field within the tube 262, and the need for more intense UV sources such as the mercury lamps 272 and 274 positioned at the opposite ends of a tube housing 275 in the opposite end plates 276 and 278 generally centered on the longitudinal axis 279 of the tube 262 behind quartz or other similar heat resistant UV transparent windows 280 and 282. Quartz windows 280 and 282 are preferred because their UV absorption is minimal, their cost is low, and their structural strength is high. The strong magnetic field is generally constant with its polarity being switched on about two second intervals by a square wave generator 283. A strong constant magnetic field seems to affect microorganisms adversely so that a complete "kill" with UV is more easily accomplished. Generally, the coatings and reflective surfaces of the inside surface 284 of the MISE tube 262 are identical to those of the MISE tube 108.

Other substances that could be substituted to create the effect caused by the incorporation of the ceramic fluorescent "repeller" thereby providing the required deterrent to virion naturally moving to the exit passage of the mise tube to avoid UV exposure, include: hydronzincite; uranium+ lithium fluoride; fluorite+europium; andesine+ europium;

orthoclase+europium; fluorite; benitoite; hydrozincite; margarosanite; scheelite; wolframite+lithium fluoride; allingite; alunogen; amethyst; ceiestite; danburite; diamond diops; dolomite; dumortierite; forsterite; gypsum; hydromagnesite; ktypeite; microcline; opal; pirssonite; plumballophane; simpsonite; and wollastonite.

A centered, highly polished nickel coated and then transparently coated conductor 285 is used in each tube 262 to reflect UV from the longitudinal axis 279 that otherwise would be a wasteful UV "hot spot", to enhance the effectiveness of the MISE tube 262. A 5000 volt alternating current is applied between the conductor 285 and the housing 275 to provide electrons to activate UV producing phosphors in the coating on the inside surface 284 of the MISE tube 262.

The pulse output flow 264 of the cavitation chambers 256 is input into the interior 286 of the tube 262, though an elbow 287 that imparts a swirl thereto to assure that no portion of the flow goes quickly into the outlet 288 and to restrict the line of sight of UV up the flow 264. Note that the outlet 288 faces opposite the swirl to further restrict direct output flow. The flow 264 is subjected to UV radiant energy inside the tube 262 as previously described. Since the UV energy must travel a relatively long distance, the outlet 288 of the MISE tube 262 is sized to be the restriction in the system 270 to assure that any organism remains in the tube 262 for at least 14 seconds so a lethal dose of UV is applied. The 14 second kill time is characteristic of a MISE tube of the dimensions as described above. As shown in FIG. 13, the MISE tube 262 also includes a drain 290 used during maintenance so that the housing 275 can be emptied and thereafter end caps 276 and 278 can be removed from the tube housing 275 without release of sewage.

The outlet flow 292 of the MISE tube 262 usually is gravity flowed in a flow channel 294 to a diluting body of water 296 such as a lake, river or the ocean. The flow channel 294 preferably provides an environment where organic bits are not provided enough energy to recombine into organisms and/or exposes them to destructive radiation, such as when instead of being a black, lightless flow channel, a solar IR filter 298 is provided along the upper surface thereof so that the flow 292 is exposed to damaging IR radiation during the daytime to prevent growth back up the channel toward the MISE tubes 262.

Figure 14:
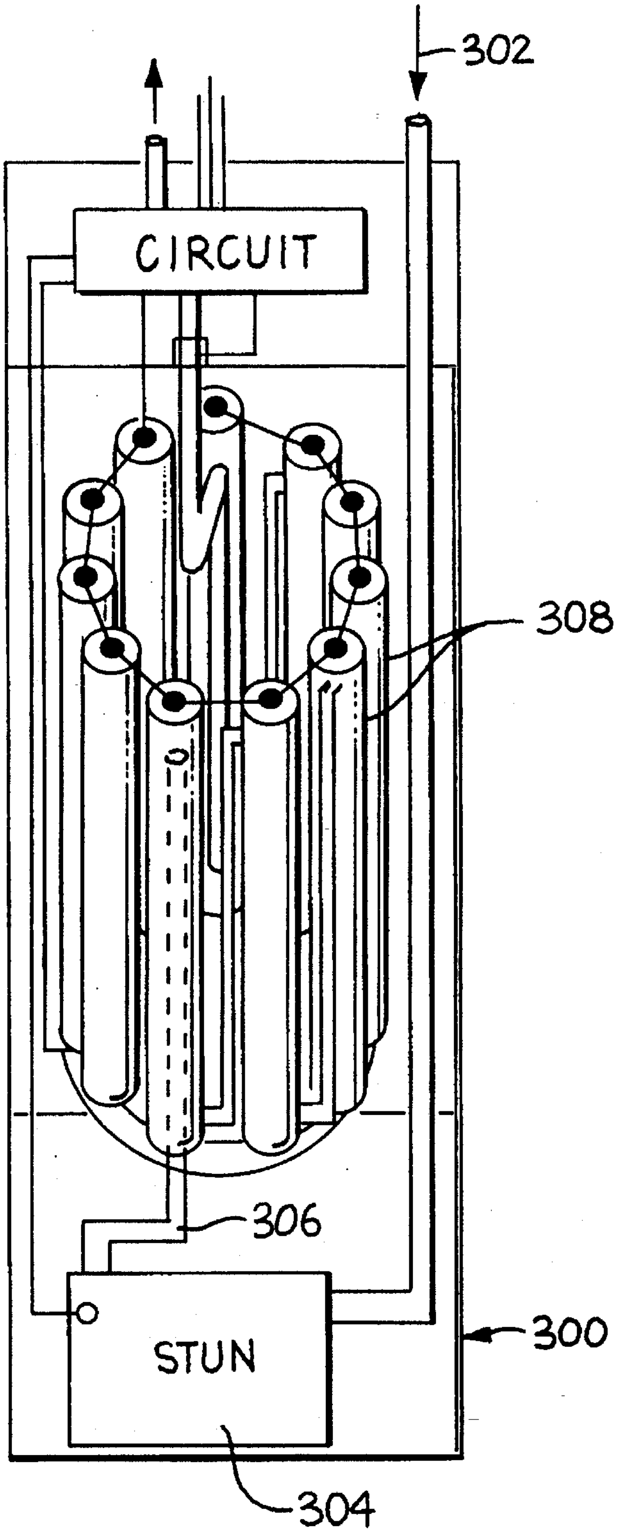
FIG. 14 is a diagrammatic view of a plurality of MISE tubes similar to that of FIG. 5 connected in series for use in an intermediate sized water treatment system.

FIG. 14 shows a stun chamber and MISE tube assembly 300 suitable for intermediate flows. The assembly 300 receives an input flow 302 from a suitable pump, the flow 302 being passed through a stunning chamber 304 similar to stunning chamber 220. The output 306 from the stunning chamber 304 is fed serially to a plurality of MISE tubes 308 constructed with the same general configuration as MISE tube 108, but employing commercial UV tubes of the longest length and most intense available. The effect of the series connected MISE tubes 308 is that organisms in the flow 302 are exposed to damaging ultraviolet radiation for a sufficient time to receive a lethal dose even though the velocity flow through the MISE tubes 308 is substantially higher than that found in system 20.

Thus, there has been shown and described novel waste water treatment systems which fulfil all of the objects and advantages sought therefore. Many changes, alterations, modifications and other uses and applications of the subject waste water treatment systems and components will become apparent to those skilled in the art after considering the specification together with the accompanying drawings. All such changes, alterations and modifications which should not depart from the spirit and scope of the invention are deemed to be covered by the invention, which is limited only by the claims that follow:

I claim:

1. A system for sterilizing water including:

a flow path for the water;

an inlet for said flow path;

an outlet for said flow path;

stun means in said flow path downstream from said inlet to apply an electrical potential across the flow path of sufficient strength to rupture cell membranes of cellular organisms thereat and to disable defense mechanisms of viral organisms to ultraviolet light; and sterilizing means positioned in said flow path downstream of said stun means and upstream of said outlet to apply a lethal frequency range and power of ultraviolet radiation to viral organisms with disabled defense mechanisms, whereby water at said outlet is sterilized.

2. The system for sterilizing water as defined in claim 1 wherein said stun means include:

a plurality of closely spaced electrodes in said flow path; and means to apply a potential between said closely spaced electrodes.

3. The system for sterilizing water as defined in claim 1 wherein said stun means include:

a plurality of closely spaced electrode plates in said flow path; and means to apply a potential between said closely spaced electrode plates.

4. The system for sterilizing water as defined in claim 3 wherein said plurality of closely spaced electrode plates in said flow path are spaced at about 254 micrometers to about 127 micrometers.

5. The system for sterilizing water as defined in claim 1 wherein said sterilizing means include:

a housing having:

an inner cylindrical surface having:

an ultraviolet reflecting coating thereon;

ultraviolet absorbing and emitting materials thereon; and ultraviolet emitting materials thereon responsive to electrons;

a source of ultraviolet energy connected to said housing to fill said housing with ultraviolet energy and electrons, and thereby impinge lethal ultraviolet energy from said source of ultraviolet energy, from said ultraviolet absorbing and emitting materials, and from said ultraviolet emitting materials on organisms therewithin to sterilize water flowing therethrough.

6. The system for sterilizing water as defined in claim 5 wherein said sterilizing means include:

a housing inlet connected to receive polluted water containing stunned viral organisms from said stun chamber;

a housing outlet through which sterilized water can leave said housing, said inner cylindrical surface adjacent said housing outlet including:

material that emits blue light to repel any viral organisms thereat.

7. The system for sterilizing water as defined in claim 1 wherein said sterilizing means include:

a housing having:

an inner cylindrical surface having:

an ultraviolet reflecting coating thereon; and ultraviolet absorbing and emitting materials thereon;

a source of ultraviolet energy connected to said housing to fill said housing with ultraviolet energy and thereby impinge lethal ultraviolet energy from said source of ultraviolet energy and from said ultraviolet absorbing and emitting materials on organisms therewithin to sterilize water flowing therethrough.

8. The system for sterilizing water as defined in claim 7 further including:

a pulse pump upstream of said stun chamber capable of forcing water in finite amounts through said stun chamber, said cavitation chamber, and said sterilizing means to assure a lethal exposure to ultraviolet, and wherein said housing includes:

a coil thereabout positioned to produce a magnetic field within said housing generally parallel to said inner cylindrical surface when electrical current is flowing thereto.

9. The system for sterilizing water as defined in claim 8 wherein said finite amounts of water are matched to flow volumes of said stun chamber, said cavitation chamber, and said sterilizing means to assure all organisms in the water are exposed to electrical potential of sufficient strength to rupture cell membranes thereof, to disable defense mechanisms of viral organisms to ultraviolet light, and so a lethal power of ultraviolet radiation is applied to viral organisms.

10. The system for sterilizing water as defined in claim 1 further including:

a cavitation chamber positioned between said stun chamber and said sterilizing means, said cavitation chamber being capable of producing acoustic energy at a first frequency to resonate in said system to assist in cleaning said stun chamber, said sterilizing means, and said cavitation chamber, and a second frequency capable of causing cavitation within said cavitation chamber to injure organisms therewithin.

11. The system for sterilizing water as defined in claim 10 further including:

an activated charcoal filter downstream of said sterilizing means.

12. The system for sterilizing water as defined in claim 10 further including:

a solids filter upstream of said stun chamber; and a settling tank upstream of said solids filter.

13. The system for sterilizing water as defined in claim 1 wherein said sterilizing means include:

a housing having:
an inner cylindrical surface having:
an ultraviolet reflecting coating thereon; and
ultraviolet absorbing and emitting materials thereon chosen from the group consisting of:
hydronzincite;
uranium+lithium fluoride;
fluorite+europium;
andesine+europium;
orthoclase+europium;
fluorite;
benitoite;
hydrozincite;
margarosanite;
scheelite;
wolframite+lithium fluoride;
allingite;
alunogen;
amethyst;
ceiestite;
danburite;
diamond;
dolomite;
dumortierite;
forsterite;
gypsum;
hydromagnesite;
ktypeite;
microcline;
opal;
pirssonite;
plumballophane;
simpsonite; and
wollastonite;

a source of ultraviolet energy connected to said housing to fill said housing with ultraviolet energy and thereby impinge lethal ultraviolet energy from said source of ultraviolet energy and from said ultraviolet absorbing and emitting materials on organisms therewithin to sterilize water flowing therethrough.

14. The system for sterilizing water as defined in claim 1 wherein said sterilizing means include:

a housing having:
an inner cylindrical surface having:
a longitudinal axis;
an ultraviolet reflecting coating thereon; and
ultraviolet absorbing and emitting materials thereon; and a source of ultraviolet energy connected to said housing extending generally along said longitudinal axis to fill said housing with ultraviolet energy and thereby impinge lethal ultraviolet energy from said source of ultraviolet energy and from said ultraviolet absorbing and emitting materials on organisms therewithin to sterilize water flowing therethrough.

15. The system for sterilizing water as defined in claim 1 wherein said sterilizing means include:

a housing having:
an inner cylindrical surface having:
an ultraviolet reflecting coating thereon;
ultraviolet absorbing and emitting materials thereon; and
ultraviolet emitting materials thereon responsive to electrons;

a high voltage electrode extending generally along the longitudinal axis of the inner housing to energize said ultraviolet emitting materials responsive to electrons; and a source of ultraviolet energy connected to said housing to fill said housing with ultraviolet energy and thereby impinge lethal ultraviolet energy from said source of ultraviolet energy, from said ultraviolet absorbing and emitting materials, and from said ultraviolet emitting materials thereon responsive to electrons on organisms therewithin to sterilize water flowing therethrough.

16. The system for sterilizing water as defined in claim 1 wherein said stun means include:

a stun housing having:
a cylindrical inner wall surface;
an inlet; and
an outlet;

at least one radial disk electrode in said flow path positioned concentrically in said cylindrical stun housing having:

an outer cylindrical electrode surface closely spaced from said cylindrical inner wall surface, said outer cylindrical electrode surface and said cylindrical inner wall surface being positioned so that all flow from said stun housing inlet to said stun housing outlet must pass therebetween; and means to apply an intense electric field between said at least one radial disk electrode and said cylindrical inner wall surface.

17. The system for sterilizing water as defined in claim 16 wherein said stun means further include:

an elongate body having:

a body cylindrical surface positioned concentrically within said cylindrical inner wall surface of said stun housing, downstream of said at least one radial disk electrode and positioned so that all flow from said stun housing inlet to said stun housing outlet must pass therebetween, said means to apply an intense electric field between said at least one radial disk electrode and said cylindrical inner wall surface also applying an intense electric field between said body cylindrical surface and said cylindrical inner wall surface.

18. The system for sterilizing water as defined in claim 1 further including:

a dark flow channel connecting said stun chamber and said sterilizing means; and a pulse pump upstream of said stun chamber capable of forcing water in finite amounts through said stun chamber, and said sterilizing means to assure a lethal exposure to ultraviolet.

19. The system for sterilizing water as defined in claim 18 further including:

a cavitation chamber positioned in said dark flow channel, said cavitation chamber being capable of producing acoustic energy at a first frequency to resonate in said system to assist in cleaning said stun chamber, said sterilizing means, and said cavitation chamber, and a second frequency capable of causing cavitation within said cavitation chamber to injure organisms therewithin.

20. The system for sterilizing water as defined in claim 1 further including:

a cooling storage tank downstream of said sterilizing means to reduce the chance that organic fragments in said flow path will recombine into viable organisms.

21. The system for sterilizing water as defined in claim 1 further including:

an IR flow channel downstream of said sterilizing means to for applying IR energy to said flow stream to reduce the chance that organic fragments in said flow path will recombine into viable organisms.

22. The system for sterilizing water as defined in claim 1 further including:

an IR flow channel downstream of said sterilizing means to for applying IR energy to said flow stream to reduce the chance that organic fragments in said flow path will recombine into viable organisms; and dilution means to space any organic fragments in said flow stream to reduce the chance that organic fragments in said flow path will recombine into viable organisms.

23. The system for sterilizing water as defined in claim 1 wherein said sterilizing means include:

a plurality of MISE devices serially positioned in said flow path.

24. A system for producing organism free water from polluted water containing living organic contamination including:

a stunning chamber including:

a stunning chamber inlet for polluted water;

a stunning chamber outlet for polluted water;

at least first and second surfaces defining at least in part a passageway positioned between said stunning chamber inlet and said stunning chamber outlet through which the polluted water flows when flowing between said stunning chamber inlet and outlet; and a high voltage supply connected to said stunning chamber first and second surfaces capable of producing an electric potential there across of sufficient magnitude to disrupt cell membranes of celled organisms positioned therebetween and to stun viral organisms positioned therebetween so such are unable to mount a strong defense against ultraviolet radiant energy; and a sterilization chamber including:

a sterilization chamber inlet connected to receive polluted water containing stunned viral organisms from said stunning chamber outlet;

a sterilization chamber outlet through which sterilized water can leave said sterilization chamber;

a housing having:

an inner cylindrical surface having:

an ultraviolet reflecting coating thereon; and ultraviolet absorbing and emitting material thereon; and a source of ultraviolet energy positioned to fill said housing with ultraviolet energy and thereby impinge lethal ultraviolet energy from said source of ultraviolet energy and from said ultraviolet absorbing and emitting material on organisms therewithin to sterilize water for flow out said sterilization chamber outlet.

25. The system for sterilizing water as defined in claim 24 wherein said stunning chamber includes:

a plurality of closely spaced electrode plates in said flow path, said first and second surfaces being facing surfaces of said plurality of closely spaced electrode plates.

26. The system for sterilizing water as defined in claim 25 wherein said first and second surfaces are spaced at about 254 micrometers to about 127 micrometers.

27. The system for sterilizing water as defined in claim 24 wherein said stunning chamber includes:

a housing having:

a cylindrical inner wall surface;

an inlet; and an outlet;

at least one radial disk electrode positioned concentrically in said cylindrical stun housing having:

an outer cylindrical electrode surface closely spaced from said cylindrical inner wall surface, said outer cylindrical electrode surface and said cylindrical inner wall surface being positioned so that all polluted water flowing from said housing inlet to said housing outlet must pass therebetween; and means to apply an intense electric potential between said at least one radial disk electrode and said cylindrical inner wall surface.

28. The system for sterilizing water as defined in claim 27 wherein said stunning chamber further includes:

an elongate body having:

a body cylindrical surface positioned concentrically within said cylindrical inner wall surface of said housing, downstream of said at least one radial disk electrode and positioned so that all flow from said housing inlet to said housing outlet must pass therebetween, said means to apply an intense electric potential between said at least one radial disk electrode and said cylindrical inner wall surface also applying an intense electric potential between said body cylindrical surface and said cylindrical inner wall surface.

29. The system for sterilizing water as defined in claim 28 wherein said elongate body is integral with said radial disk electrode.

30. The system for sterilizing water as defined in claim 25 wherein said inner cylindrical surface includes:

phosphorescent ultraviolet emitting materials thereon, said sterilization chamber further including:

means to energize said phosphorescent ultraviolet emitting materials.

31. The system for sterilizing water as defined in claim 30 wherein said sterilization chamber includes:

a housing inlet connected to receive polluted water containing stunned viral organisms from said stunning chamber and pointed to establish a swirl of polluted water adjacent said inner cylindrical surface;

a housing outlet through which sterilized water can leave said housing, said ultraviolet absorbing and emitting materials on said inner cylindrical surface adjacent said housing outlet including;

material that emits blue light to repel any viable viral organisms thereat.

32. The system for sterilizing water as defined in claim 24 wherein said ultraviolet absorbing and emitting materials thereon are chosen from the group consisting of:

hydronzincite;
uranium+lithium fluoride;
fluorite+europium;
andesine+europium;
orthoclase+europium;
fluorite;
benitoite;
hydrozincite;
margarosanite;
scheelite;
wolframite+lithium fluoride;
allingite;
alunogen;
amethyst;
ceiestite;
danburite;
diamond;
dolomite;
dumortierite;
forsterite;
gypsum;
hydromagnesite;
ktypeite;
microcline;
opal;
pirssonite;
plumballophane;
simpsonite; and
wollastonite.

33. The system for sterilizing water as defined in claim 24 wherein said housing has:

a longitudinal axis, said source of ultraviolet energy being a plasma source and sealably connected to said housing and extending generally along said longitudinal axis to fill said housing with ultraviolet energy and thereby impinge lethal ultraviolet energy from said source of ultraviolet energy and from said ultraviolet absorbing and emitting materials on organisms therewithin.

34. The system for sterilizing water as defined in claim 24 wherein said housing includes:

a coil thereabout capable of creating a magnetic field within said housing when an electrical current is flowing therethrough;

first and second ends;

a longitudinal axis extending between said first and second ends,a high voltage electrode extending generally along the longitudinal axis of the inner housing; and a ultraviolet reflective electrode to provide high voltage alternating potential between said high voltage electrode and said housing, said ultraviolet absorbing and emitting materials being responsive thereto to fluoresce ultraviolet energy, said source of ultraviolet energy being ultraviolet lamps positioned at said first and second ends of said housing to fill said housing with ultraviolet energy and thereby impinge lethal ultraviolet energy from said source of ultraviolet energy and from said ultraviolet absorbing and emitting materials on organisms therewithin to sterilize water flowing therethrough.

35. A molecularly implanted simulated emitter device for inactivation of microorganisms including:

a housing having:

a first inner surface having:

ultraviolet reflecting material thereon; and at least one ultraviolet absorbing and emitting material capable of absorbing ultraviolet in one range of wavelengths and emitting ultraviolet at other range of ultraviolet wavelengths therefrom;

a housing inlet adapted to receive polluted water containing viral organisms;

a housing outlet through which sterilized water can leave said housing, said housing inlet and outlet being positioned with respect to said first inner surface so that any flow between said housing inlet and outlet is exposed to said first inner surface; and a source of ultraviolet energy positioned with respect to said housing to fill said housing with ultraviolet energy in said one range of wavelengths.

36. The molecularly implanted simulated emitter device for inactivation of microorganisms as defined in claim 35 including:

at least one absorbing and emitting material on said inner cylindrical surface adjacent said housing outlet that emits blue light in response to absorption of ultraviolet energy.

37. The molecularly implanted simulated emitter device for inactivation of microorganisms as defined in claim 35 wherein said housing first inner surface is cylindrical surface having:

a longitudinal axis; and wherein said source of ultraviolet energy is sealably connected to said housing and extends generally along said longitudinal axis of the inner housing.

38. The molecularly implanted simulated emitter device for inactivation of microorganisms as defined in claim 35 wherein housing includes:

first and second ends;

a second ultraviolet emitting material capable of response to high voltage alternating potential to emit ultraviolet at other range of ultraviolet wavelengths therefrom;

a ultraviolet reflective electrode extending along the longitudinal axis of the inner housing; and means to provide high voltage alternating potential between said ultraviolet reflective electrode and said housing, and wherein said source of ultraviolet energy includes;

a pair of ultraviolet lamps positioned at said first and second ends of said housing.

39. The molecularly implanted simulated emitter device for inactivation of microorganisms as defined in claim 35 including:

at least one absorbing and emitting material on said inner cylindrical surface adjacent said housing outlet that emits blue light in response to absorption of ultraviolet energy.

40. The molecularly implanted simulated emitter device for inactivation of microorganisms as defined in claim 35 wherein said at least one ultraviolet absorbing and emitting material is chosen from the group consisting of:

hydronzincite;

uranium+lithium fluoride;

fluorite+europium;

andesine+europium;

orthoclase+europium;

fluorite;

benitoite;

hydrozincite;

margarosanite;

scheelite;

wolframite+lithium fluoride;

allingite;

alunogen;

amethyst;

ceiestite;

danburite;

diamond diops;

dolomite;

dumortierite;

forsterite;

gypsum;

hydromagnesite;

ktypeite;

microcline;

opal;

pirssonite;

plumballophane;

simpsonite; and wollastonite.

* * * * *